United States Patent [19]

Creger

[11] Patent Number: 5,177,106
[45] Date of Patent: Jan. 5, 1993

[54] 4-AMINO SUBSTITUTED PHENOXYALKYL CARBOXYLIC ACID, ESTER, AND ALCOHOL DERIVATIVES AS ANTIHYPERCHOLESTEROLEMIC AND ANTIATHEROSCLEROTIC AGENTS

[75] Inventor: Paul L. Creger, Ann Arbor, Mich.

[73] Assignee: Warner-Lambert Company, Morris Plains, N.J.

[21] Appl. No.: 718,748

[22] Filed: Jun. 21, 1991

[51] Int. Cl.$^5$ .................. A61K 31/215; C07C 69/612
[52] U.S. Cl. .................................... 514/538; 514/542; 560/9; 560/12; 560/34
[58] Field of Search ............... 560/12, 9, 34; 514/538, 514/542

[56] References Cited

U.S. PATENT DOCUMENTS 4,737,512  4/1988  Hoefle ................................ 514/417
4,882,357  11/1989 Creger et al. ..................... 514/622

FOREIGN PATENT DOCUMENTS 0130077  1/1985  European Pat. Off. .
0270929  6/1988  European Pat. Off. .

OTHER PUBLICATIONS

*Chemical Abstracts* vol. 102 No. 19, abstract 166457(d) May, 1985.

Primary Examiner—Mary C. Lee
Assistant Examiner—Jacqueline Haley
Attorney, Agent, or Firm—Francis J. Tinney

[57] ABSTRACT

Novel 4-amino substituted phenoxyalkyl carboxylic acid, ester, and alcohol derivatives are described, as well as methods for the preparation and pharmaceutical composition of same, which are useful in preventing the intestinal absorption of cholesterol and thus are useful in the treatment of hypercholesterolemia and atherosclerosis.

3 Claims, No Drawings

4-AMINO SUBSTITUTED PHENOXYALKYL CARBOXYLIC ACID, ESTER, AND ALCOHOL DERIVATIVES AS ANTIHYPERCHOLESTEROLEMIC AND ANTIATHEROSCLEROTIC AGENTS

BACKGROUND OF THE INVENTION

The present invention relates to novel substituted 4-aminosubstituted phenoxy alkyl carboxylic acid, ester, and alcohol derivatives useful as pharmaceutical agents, to methods for their production, to pharmaceutical compositions which include these compounds and a pharmaceutically acceptable carrier, and to a pharmaceutical method of treatment. More particularly, the novel compounds of the present invention lower low density lipoprotein cholesterol (LDL) and elevate high density lipoprotein cholesterol (HDL). Both of these effects afford protection from coronary heart disease.

The atheromatous plaque, which is the characteristic lesion of atherosclerosis, results from deposition of plasma lipids, mainly cholesteryl esters, in the intima of the arterial wall. Progressive enlargement of the plaque leads to arterial constriction and ultimately coronary heart disease. Two recent clinical trials have shown a causal relationship between serum levels of LDL- and HDL-cholesterol and coronary heart disease.

In 1984, the Lipid Research Clinics-Coronary Prevention Trial (LRC-CPPT) demonstrated for the first time that lowering LDL cholesterol would reduce coronary heart disease. Very recently the results of a 5-year, 4,081-patient clinical trial published in the *New England Journal of Medicine* 317:1237-145 (1987) demonstrated that the lipid regulating drug, gemfibrozil, reduced the rate of heart attack and sudden cardiac death by 34% in patients with elevated cholesterol levels. Gemfibrozil both lowers LDL and elevates HDL; but if the results from the LRC-CPPT study are utilized to estimate the expected reduction in incidence of heart attack and heart disease due to lowering of LDL, it amounts to approximately one-half of the effect actually observed. Thus, there appears to be little doubt as to the benefit of elevating HDL.

The compounds of this invention combine two mechanisms of action to achieve their improved activity in lowering LDL and elevating HDL. Not only do they show the same effects as gemfibrozil but, in addition, they inhibit the enzyme acyl-CoA:cholesterol acyltransferase (ACAT).

Dietary cholesterol is absorbed from the intestinal lumen as free cholesterol which must be esterified with fatty acids. This reaction is catalyzed by ACAT. The resulting cholesteryl esters are packaged into the chylomicrons which are secreted into the lymph. Inhibitors of ACAT not only prevent absorption of dietary cholesterol but also prevent the reabsorption of cholesterol which has been released into the intestine through endogenous regulatory mechanisms, thus lowering LDL cholesterol levels and ultimately preventing the further development of atherosclerosis.

The present compounds have been chosen for their ability to lower LDL and elevate HDL and also to inhibit ACAT, and thus they possess two different mechanisms of action that complement each other. Thus, gemfibrozil speeds up the metabolism of LDL in the liver, and the excess cholesterol is released into the intestines via the bile. Normally a portion of this cholesterol is reabsorbed and ultimately recirculated in the form of new LDL. However, this is prevented in the presence of an ACAT inhibitor.

SUMMARY OF THE INVENTION

Accordingly, the present invention is a novel compound of Formula I

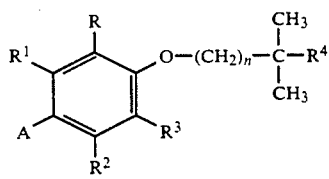

wherein A is
—NH$_2$,
—NO$_2$,

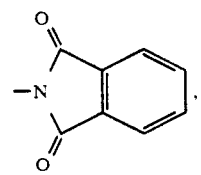

—NH—SO$_2$—R$^5$ wherein R$^5$ is alkyl of from one to twenty carbon atoms, or aryl, or benzyl,

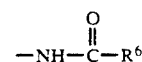

wherein R$^6$ is alkyl of from one to twenty carbon atoms, or aryl, or

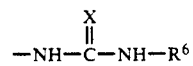

wherein X is O or S and R$^6$ is as defined above;

R, R$^1$, R$^2$, and R$^3$ are each independently hydrogen or alkyl of from one to six carbon atoms provided at least two of R, R$^1$, R$^2$, or R$^3$ are alkyl of from one to six carbon atoms;

n is an integer of 3, 4, 5, or 6;

R$^4$ is —CO$_2$R$^7$ wherein R$^7$ is hydrogen, alkyl of from one to six carbon atoms, or benzyl, or —CH$_2$OH; or a pharmaceutically acceptable salt thereof.

Additionally, the present invention is directed to a novel method of treating hypercholesterolemia or atherosclerosis comprising administering to a mammal in need of such treatment an acyl-coenzyme A:cholesterol acyltransferase-inhibitory effective amount of a compound of Formula I in unit dosage form.

Also, the present invention is directed to a pharmaceutical composition for treating hypercholesterolemia or atherosclerosis comprising an acyl-coenzyme A:-cholesteryl acyltransferase-inhibitory effective amount of a compound of Formula I in combination with a pharmaceutically acceptable carrier.

Finally, the present invention is directed to methods for production of a compound of Formula I.

DETAILED DESCRIPTION OF THE INVENTION

In the compounds of Formula I, the term "alkyl" means a straight or branched hydrocarbon radical having from one to twenty carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl, undecyl, dodecyl, tridecyl, tetradecyl, pentadecyl, hexadecyl, heptadecyl, octadecyl, nonadecyl, eicosyl, and the like.

"Alkoxy" and "thioalkoxy" are O-alkyl or S-alkyl of from one to twenty carbon atoms as defined above for "alkyl".

The term "aryl" means an aromatic radical which is a phenyl group or a naphthyl group, unsubstituted or substituted by one to four substituents selected from alkyl as defined above, alkoxy as defined above, thioalkoxy as defined above, hydroxy or halogen.

"Halogen" is fluorine, chlorine, bromine, or iodine.

"Alkali metal" is a metal in Group IA of the periodic table and includes, for example, lithium, sodium, potassium, and the like.

"Alkaline-earth metal" is a metal in Group IIA of the periodic table and includes, for example, calcium, barium, strontium, magnesium, and the like.

The compounds of Formula I are capable of further forming pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, phosphorous and the like, as well as the salts derived from nontoxic organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate and the like. Also contemplated are salts of amino acids such as arginate and the like and gluconate, galacturonate (see, for example, Bergs S. M., et al, "Pharmaceutical Salts," *Journal of Pharmaceutical Science*, Vol. 66, pages 1–19 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free bases for purposes of the present invention.

Pharmaceutically acceptable base addition salts are formed with metals or amines such as alkali and alkaline earth metals or organic amines. Examples of metals used as cations are sodium, potassium, magnesium, calcium and the like. Examples of suitable amines are N,N'-dibenzylethylenediamine, chloroprocaine, choline, diethanolamine, ethylenediamine, N-methylglucamine, and procaine (see, for example, Berge S. M., et al, *Journal of Pharmaceutical Science*, Vol. 66, pages 1–19 (1977)).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acids for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

A preferred compound of Formula I is one wherein R, $R^1$, $R^2$, and $R^3$ are each independently hydrogen or methyl provided at least two of R, $R^1$, $R^2$, or $R^3$ are methyl.

Another preferred embodiment is a compound of Formula I wherein R, $R^1$, $R^2$, and $R^3$ are each independently hydrogen or methyl provided at least two of R, $R^1$, $R^2$, or $R^3$ are methyl and n is an integer of 3.

Particularly valuable are:

5-(2,5-Dimethyl-4-nitrophenoxy)-2,2-dimethylpentanoic acid, methyl ester;

5-(4-amino-2,5-dimethylphenoxy)-2,2-dimethylpentanoic acid, methyl ester, monohydrochloride;

5-[4-(1,3-Dihydro-1,3-dioxo-2H-isoindol-2-yl)-2,5-dimethylphenoxy]-2,2-dimethylpentanoic acid, methyl ester;

5-[2,5-Dimethyl-4-[[(4-methylphenyl)sulfonyl]amino]phenoxy]-2,2-dimethylpentanoic acid, methyl ester;

5-[4-[(Hexadecylsulfonyl)amino]-2,5-dimethylphenoxy]-2,2-dimethylpentanoic acid, methyl ester;

5-[2,5-Dimethyl-4-[[(phenylmethyl)sulfonyl]-amino]-phenoxy]-2,2-dimethylpentanoic acid, methyl ester;

5-[4-[[(4-Fluorophenyl)sulfonyl]amino]-2,5-dimethylphenoxy]-2,2-dimethylpentanoic acid, methyl ester;

5-[2,5-Dimethyl-4-[(2-naphthalenylsulfonyl)-amino]-phenoxy]-2,2-dimethylpentanoic acid, methyl ester;

5-[4-[[2,5-Dichlorophenyl)sulfonyl]amino]-2,5-dimethylphenoxy]-2,2-dimethylpentanoic acid, methyl ester;

2,2-Dimethyl-5-[2,5-dimethyl-4-[[(2,4,6-trimethylphenyl)sulfonyl]amino]phenoxy]pentanoic acid, methyl ester;

5-[4-(Benzoylamino)-2,5-dimethylphenoxy]-2,2-dimethylpentanoic acid, methyl ester;

5-[[2,5-Dimethyl-4-[(methylsulfonyl)amino]-phenoxy]-2,2-dimethylpentanoic acid, methyl ester;

5-[4-[[(4-Methoxyphenyl)sulfonyl]amino]-2,5-dimethylphenoxy]-2,2-dimethylpentanoic acid, methyl ester;

5-[4-[[[(2,4-Difluorophenyl)amino]carbonyl]-amino]-2,5-dimethylphenoxy]-2,2-dimethylpentanoic acid, methyl ester;

5-[4-[[[2,6-Bis(1-methylethyl)phenyl]amino]-carbonyl]amino]-2,5-dimethylphenoxy]-2,2-dimethylpentanoic acid, methyl ester;

5-[2,5-Dimethyl 4 [[(phenylamino)thioxomethyl]-amino]phenoxy]-2,2-dimethylpentanoic acid, methyl ester; and 5-[4-(Acetylamino)-2,5 dimethylphenoxy]-2,2-dimethylpentanoic acid, methyl ester; or a pharmaceutically acceptable salt thereof.

The compounds of the present invention were tested for their ability to inhibit the esterification of cholesterol by the enzyme acyl-CoA:cholesterol acyltransferase (ACAT). The data in the table below is expressed as $IC_{50}$ values, i.e., the concentration of test compound required to inhibit cholesteryl oleate formation to 50% of control. The data in the table shows the ability of representative compounds of the present invention to potently inhibit ACAT.

The in vitro test employed is more fully described in Field, F. J. and Salome, R. G., *Biochemica et Biophysica Acta*, Volume 712, pages 557-570 (1982). The assay evaluates the ability of a test compound to inhibit the esterification of cholesterol using endogenous cholesterol of a rabbit intestinal microsomal fraction and exogenous $^{14}C$-oleoyl-CoA as reactants.

Additionally, the elevation of HDL is reported in the table as a ratio of the elevation of HDL effected by a dose of 50 mg/kg of the test drug divided by the elevation of HDL effected by a 50 mg/kg dose of gemfibrozil which is used as a control in each experiment.

$$HDL \text{ elevation} = \frac{\Delta \ HDL \text{ test drug}}{\Delta \ HDL \text{ gemfibrozil}}$$

Thus, a figure of 1 means that the test drug was as effective as gemfibrozil in elevating HDL. Values greater than 1 suggest that the test drug is more effective than gemfibrozil. The test procedure is described in U.S. Pat. No. 4,413,011, which is herein incorporated by reference.

TABLE 1

| Biological Activity of Compounds of Formula I | | | |
|---|---|---|---|
| Example Number | Compound | $IC_{50}$ ($\mu$ moles) | $\frac{\Delta \text{ HDL Test Compound}}{\Delta \text{ HDL Gemfibrozil}}$ |
| 5 | 5-[4-(Hexadecylsulfonyl)amino]-2,5-dimethylphenoxy]-2,2-dimethyl-pentanoic acid, methyl ester | 74 | 0.8 |
| 12 | 5-[[2,5-Dimethyl-4-[(methylsulfonyl)-amino]phenoxy]-2,2-dimethylpentanoic acid, methyl ester | 69 | 1.5 |
| 16 | 5-[2,5-Dimethyl-4-[[(phenylamino)-thioxomethyl]amino]phenoxy]-2,2-dimethylpentanoic acid, methyl ester | 28 | 0.9 |

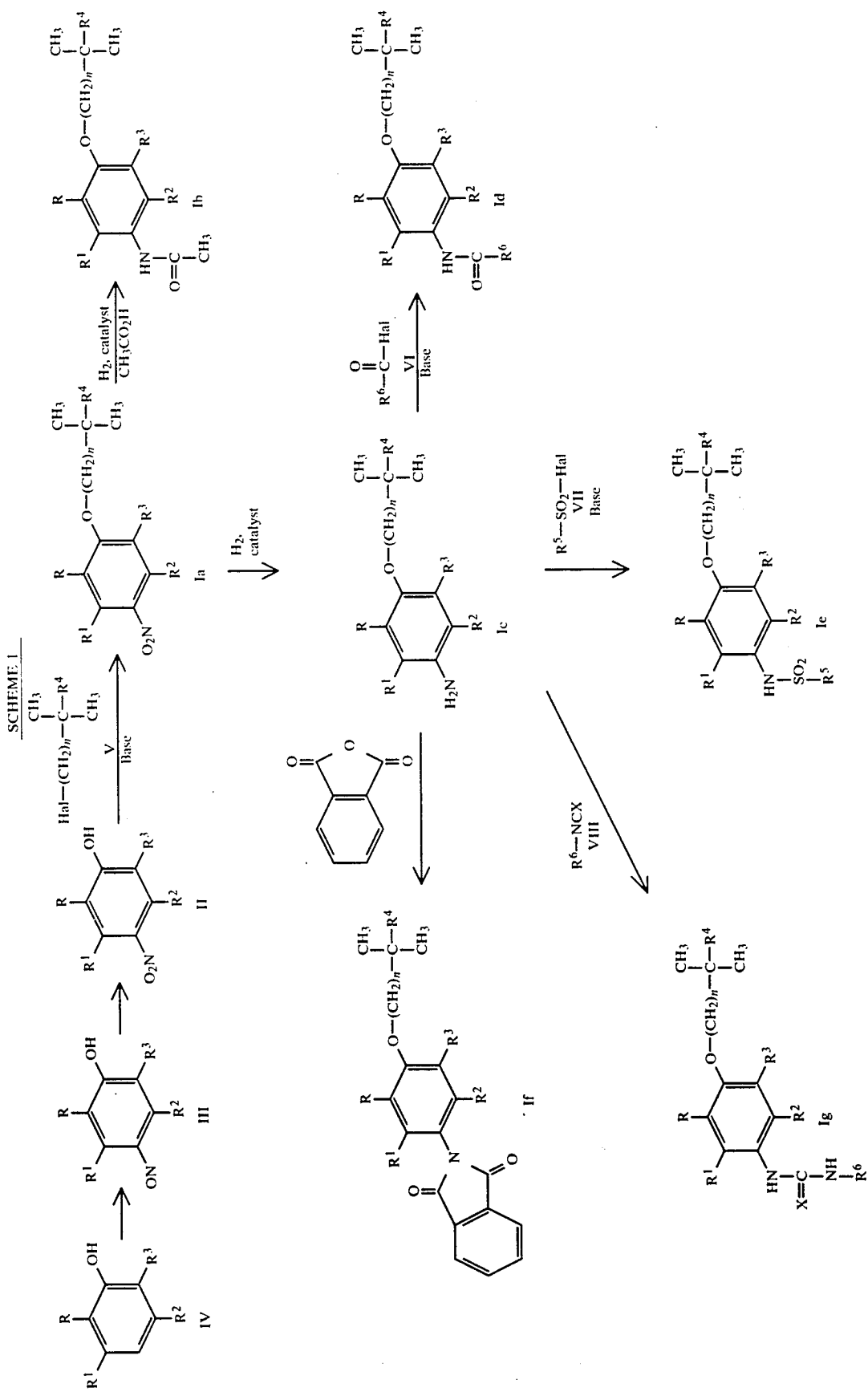

The compounds of the present invention may be prepared as outlined in Scheme I.

Thus, a compound of Formula Ia wherein R, $R^1$, $R^2$, and $R^3$ are each independently hydrogen or alkyl of from one to six carbon atoms provided at least two of R, $R^1$, $R^2$, or $R^3$ are alkyl of from one to six carbons; n is an integer of 3, 4, 5, or 6; $R^4$ is $-CO_2R^7$ wherein $R^7$ is hydrogen, alkyl, of from one to six carbon atoms, or benzyl, or $-CH_2OH$; or a pharmaceutically acceptable salt thereof may be prepared by reacting a compound of Formula II wherein R, $R^1$, $R^2$, and $R^3$ are as defined above with a compound of Formula V wherein Hal is halogen and n and $R^4$ are as defined above in the presence of a base such as an alkali metal carbonate or hydroxide, an alkaline earth metal carbonate or hydroxide, for example, potassium carbonate, sodium carbonate and the like and a solvent such as, for example, acetonitrile and the like at about room temperature to about the reflux temperature of the solvent for about 8 hours to about 24 hours to afford a compound of Formula Ia. Preferably, the reaction is carried out in the presence of potassium carbonate and acetonitrile at about reflux temperature for about 18 hours.

A compound of Formula Ib wherein R, $R^1$, $R^2$, $R^3$, $R^4$, and n are as defined above may be prepared by reducing a compound of Formula Ia wherein R, $R^1$, $R^2$, $R^3$, $R^4$, and n are as defined above with iron powder and glacial acetic acid to afford a compound of Formula Ib.

A compound of Formula Ic wherein R, $R^1$, $R^2$, $R^3$, $R^4$, and n are as defined above may be prepared by reacting a compound of Formula Ia wherein R, $R^1$, $R^2$, $R^3$, $R^4$, and n are as defined above with hydrogen in the presence of a catalyst such as, for example, palladium on carbon and the like and a solvent such as, for example, methanol and the like to afford a compound of Formula Ic. Preferably, the reaction is carried out in the presence of about 5% palladium on carbon in methanol.

A compound of Formula Id wherein $R^6$ is alkyl of from one to twenty carbon atoms, or aryl and R, $R^1$, $R^2$, $R^3$, $R^4$, and n are as defined above may be prepared by reacting a compound of Formula Ic wherein R, $R^1$, $R^2$, $R^3$, $R^4$, and n are as defined above with a compound of Formula VI wherein $R^6$ and Hal are as defined above in the presence of a base such as, for example, triethylamine and the like and a solvent such as, for example, methylene chloride and the like at about 0° C to about 25° C to afford a compound of Formula Id. Preferably, the reaction is carried out in the presence of triethylamine and methylene chloride at about 0° C.

A compound of Formula Ie wherein $R^5$ is alkyl of from one to twenty carbon atoms, aryl, or benzyl and R, $R^1$, $R^2$, $R^3$, $R^4$, and n are as defined above may be prepared by reacting a compound of Formula Ic with a compound of Formula VII wherein $R^5$ and Hal are as defined above using the methodology used to prepare a compound of Formula Id from a compound of Formula Ic and Formula VI.

A compound of Formula If wherein R, $R^1$, $R^2$, $R^3$, $R^4$, and n are as defined above may be prepared by reacting a compound of Formula Ic with phthalic anhydride in the presence of a solvent such as, for example, toluene and the like at about 25° C to about the reflux temperature of the solvent for about 1 hour to about 24 hours to afford a compound of Formula If. Preferably, the reaction is carried out in toluene at about reflux for about 2 hours.

A compound of Formula Ig wherein X is O or S and R, $R^1$, $R^2$, $R^3$, $R^4$, $R^6$, and n are as defined above may be prepared by reacting a compound of Formula Ic wherein R, $R^1$, $R^2$, $R^3$, $R^4$, and n are as defined above with a compound of Formula VIII wherein X and $R^6$ are as defined above in the presence of a solvent such as, for example, toluene, tetrahydrofuran and the like at about 25° C. to about the reflux temperature of the solvent for about 1 hour to about 24 hours to afford a compound of Formula Ig. Preferably, the reaction is carried out in toluene at about 50° C. for about 18 hours when X is O and in tetrahydrofuran at about reflux for about 1 hours when X is S.

A compound of Formula II wherein R, $R^1$, $R^2$, and $R^3$ are as defined above may be prepared by reacting a compound of Formula IV wherein R, $R^1$, $R^2$, and $R^3$ are as defined above with sulfuric acid in glacial acetic acid followed by the addition of an aqueous solution of sodium nitrite at about 5° to 10° C. to afford the nitroso derivative of Formula III wherein R, $R^1$, $R^2$, and $R^3$ are as defined above, which may be optionally isolated or used without further purification. Thus, reaction of a compound of Formula III with 70% solution of nitric acid and warming to about 45° C.±5° C. affords a compound of Formula II.

Compounds of Formula IV, Formula V, Formula VI, Formula VII, and Formula VIII are either known or capable of being prepared by methods known in the art.

The compounds of the present invention can be prepared and administered in a wide variety of oral and parenteral dosage forms. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active compound is mixed with the carrier having the necessary binding properties in suitable proportions and compacted in the shape and size desired.

The powders and tablets preferably contain from 5% of 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted shortly before use to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 50 mg to 1500 mg, preferably 200 mg to 500 mg, according to the particular application and the potency of the active component. The composition can, if desired, also contain other compatible therapeutic agents.

The dosage range for a 70-kg mammal is from about 1 mg/kg to about 100 mg/kg of body weight per day or preferably about 3 mg/kg to about 15 mg/kg of body weight per day when the compounds of the present invention are used therapeutically as antihypercholesterolemic and antiatherosclerotic agents. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventor's preferred methods for preparing the compounds of the invention.

EXAMPLE 1

5-(2,5-Dimethyl-4-nitrophenoxy)-2,2-dimethylpentanoic acid, methyl ester

A mixture of 16.7 g (100 mmol) of 4-nitro-2,5-xylenol, 24.5 g (110 mmol) of 5-bromo-2,2-dimethylvaleric acid, methyl ester (U.S. Pat. No. 4,665,226) and 15.3 g (110 mmol) of anhydrous potassium carbonate in 200 mL of acetonitrile is stirred at reflux for 18 hours overnight. The inorganic solid is removed, washed thoroughly with fresh acetonitrile and the filtrate is evaporated. The solid residue is stirred with a mixture of diethyl ether and 100 mL of 2N potassium hydroxide solution. The aqueous layer is removed and the organic layer washed with 50 mL of 2N potassium hydroxide solution, brine, dried, and evaporated. The crystalline residue is taken up in hexane (hot), treated with charcoal to assist in removal of some insoluble material, concentrated to 200 mL, and cooled to afford 18.2 g of the title compound as pale yellow needles; mp 73°-75° C.

EXAMPLE 2

5-(4-Amino-2,5-dimethylphenoxy)-2,2-dimethylpentanoic acid, methyl ester, monohydrochloride A solution of 5-(2,5 dimethyl-4 nitrophenoxy)-2,2-dimethylpentanoic acid, methyl ester (Example 1) (4.6 g, 15 mmol) and 0.5 g of 5% palladium on carbon in 100 mL methanol is shaken under 3 atmospheres of hydrogen until hydrogen absorption is complete. The catalyst is removed and the methanol is removed on a rotary evaporator and the residue taken up in toluene, which is evaporated to afford the free base. The hydrochloride salt is prepared by treatment of the free base in anhydrous diethyl ether with excess isopropanolic hydrogen chloride and removal of the solvents followed by taking up the residue in tetrahydrofuran and crystallization by addition of isopropyl ether. Recrystallization from isopropyl ether-chloroform (5:1) affords the hydrochloride salt as a grey solid; mp 164°-166° C.

EXAMPLE 3

5-[4-(1,3 Dihydro 1,3-dioxo-2H-isoindol-2-yl)-2,5-dimethylphenoxy]-2,2-dimethylpentanoic acid, methyl ester A solution of 2.8 g (10 mmol) of 5-(4-amino-2,5-dimethylphenoxy)-2,2-dimethylpentanoic acid, methyl ester as the free base (Example 2) and 1.5 g (10 mmol) of phthalic anhydride in 100 mL of toluene is stirred at reflux beneath a phase separating head for 2 hours. The solvent is removed and on standing a red brown oil crystallizes. Recrystallization from isoctaneisopropyl ether with the addition of charcoal affords 2.8 g of the title compound as pale pink crystals; mp 109°-111° C.

EXAMPLE 4

5-2,5-Dimethyl-4-[[(4-methylphenyl)sulfonyl]amino]-phenoxy]-2,2-dimethylpentanoic acid, methyl ester A solution of 2.9 g (15.5 mmol) of para-toluenesulfonyl chloride in 25 mL of methylene chloride is added over 10 minutes at 0° C. to a solution of 5-(4-amino-2,5-dimethylphenoxy)-2,2-dimethylpentanoic acid, methyl ester as the free base (Example 2) (4.3 g, 15.5 mmol) and 3.0 g (2×15.5 mmol) of triethylamine in 125 mL of methylene chloride. When the addition is complete, the ice bath is removed and the solution is permitted to stir at ambient temperature for 24 hours.

At the conclusion of the reaction period, the solution is washed with 2×50 mL of 2N hydrochloric acid solution, 2×50 mL of 2N potassium hydroxide solution, water, dried (magnesium sulfate), and evaporated leaving 7.1 g of crude residue. The crude residue is taken up in 200 mL of isopropyl ether with the addition of charcoal, concentrated to 100 mL, and 25 mL of hexane is added. Then the solution is seeded and finally refrigerated. The title compound is obtained as an off-white solid, 5.5 g; mp 100°–102° C.

In a process analogous to Example 4 using appropriate starting materials, the corresponding compounds of Formula I (Example 5 to 11) are prepared as follows:

EXAMPLE 5

5-4-[(Hexadecylsulfonyl)amino1-2,5-dimethylphenoxy1-2,2-dimethylpentanoic acid, methyl ester; mp 71°–72° C.

EXAMPLE 6

5-[2,5-Dimethyl-4-[[(phenylmethyl)sulfonyl]amino]-phenoxy]-2,2-dimethylpentanoic acid, methyl ester; infrared inspectrum (IR) (KBr) (C=0) 1730 cm$^{-1}$.

EXAMPLE 7

5-[4 [[(4-Fluorophenyl)sulfonyl]amino1-2,5-dimethyl-phenoxy]-2,2 dimethylpentanoic acid, methyl ester; IR (KBr) (C=0) 1730 cm$^{-1}$.

EXAMPLE 8

5-2,5-Dimethyl-4-[(2-naphthalenylsulfonyl)amino]-phenoxy 2,2-dimethylpentanoic acid, methyl ester; IR (KBr) (C=0) 1729 cm$^{-1}$.

EXAMPLE 9

5-4-[2,5-Dichlorophenyl)sulfonyl]amino]-2,5-dimethyl-phenoxy]-2,2-dimethylpentanoic acid, methyl ester; mp 77°–80° C.

EXAMPLE 10

2,2-Dimethyl-5-2,5 dimethyl-4-[[(2,4,6-trimethyl-phenyl)sulfonyl]amino]phenoxy]pentanoic acid, methyl ester; mp 90°–92° C.

EXAMPLE 11

5-4-(Benzoylamino)-2,5-dimethylphenoxy]-2,2-dimethylpentanoic acid, methyl ester; mp 151°–152° C.

EXAMPLE 12

5-[[2,5-Dimethyl-4-(methylsulfonyl)amino[phenoxy]-2,2-dimethylpentanoic acid, methyl ester 5-(4-Amino-2,5-dimethylphenoxy)-2,2-dimethylpentanoic acid, methyl ester as the free base (Example 2) (5.6 g, 20 mmol) is dissolved in 100 mL of methylene dichloride and 4.0 g (2×20 mmol) of triethylamine is added and the solution is cooled to 0° C. in an ice-salt bath. Finally, a solution of 3.0 g (20 mmol) of methanesulfonyl chloride in about 5 mL of methylene chloride is added in 4 portions over 5 minutes and the solution is stirred until the ice melts and the solution reaches ambient temperature. After 2 days the red solution is diluted with diethyl ether, and the solution is washed with 2×100 mL of water, dried (magnesium sulfate), and the solvent is evaporated leaving 7.5 g of the crude methanesulfonamide. On standing the precipitate crystallizes. Recrystallization from 20 mL of acetonitrile in the presence of charcoal affords after refrigeration 4.6 g of the title compound; mp 106°–108° C.

EXAMPLE 13

5-[4-[[(4 Methoxyphenyl)sulfonyl]amino]-2,5-dimethyl-phenoxy]-2,2-dimethylpentanoic acid, methyl ester A solution of 2.2 g (12.5 mmol) of para-methoxybenzenesulfonyl chloride in 10 mL of tetrahydrofuran is added over 10 minutes at 0° C. to a solution of 3.5 g (12.5 mmol) of 5-(4-amino-2,5-dimethylphenoxy)-2,2-dimethylpentanoic acid, methyl ester as the free base (Example 2) and 2.5 g (2×12.5 mmol) of triethylamine in 40 mL of tetrahydrofuran. The ice bath is removed and the solution is permitted to stir at ambient temperature for 24 hours. The triethylammonium chloride is removed by filtration, the solvent is removed; the residue is taken up in diethyl ether, and the solution washed with 2×25 mL of 2N hydrochloric acid solution, brine, dried (magnesium sulfate), and evaporated leaving 5.0 g of a colored oil which crystallizes on standing. Recrystallization from 35 mL of isopropyl ether in the presence of charcoal affords 3.3 g of the title compound as off-white crystals; mp 90°–92° C.

EXAMPLE 14

5-[4-[[[(2,4-Difluorophenyl)amino]carbonyl]amino1-2,5-dimethylphenoxy]-2,2-dimethylpentanoic acid, methyl ester 5-(4-Amino-2,5-dimethylphenoxy)-2,2-dimethylpentanoic acid, methyl ester as the free base (Example 2) (4.15 g, 15 mmol) in 50 mL of toluene, 2.33 g (15 mmol) of 2,4-difluorophenyl isocyanate is added and the solution is stirred at 50° C. for 18 hours overnight. The solid mixture is evaporated on a rotary evaporator; the precipitate is taken up in acetonitrile, treated with charcoal, filtered, evaporated, and the residual, crystalline precipitate is recrystallized from 70 mL of toluene: 50 mL of isooctane to afford 5.7 g of the title compound as a slight pink solid; mp 152°–153° C.

In a process analogous to Example 14 using appropriate starting materials, the corresponding compound of Formula I (Example 15) is prepared as follows:

EXAMPLE 15

5-[4-[[[[2,6 Bis(1-methylethyl)phenyl]amino]carbonyl]-amino]-2,5-dimethylphenoxy]-2,2-dimethylpentanoic acid, methyl ester; mp 184°–185.5° C.

EXAMPLE 16

5-2,5-Dimethyl-4- phenylamino)thioxomethyl]amino]-phenoxy]-2,2-dimethylpentanoic acid, methyl ester A mixture of 3.5 g (12.5 mmol) of 5-(4-amino-2,5-dimethylphenoxy)-2,2-dimethylpentanoic acid, methyl ester as the free base (Example 2) and 1.7 g (12.5 mmol) of benzene isothiocyanate in 50 mL of tetrahydrofuran is stirred at reflux for 1 hours, then stirred at ambient temperature for 24 hours. The solvent is evaporated; the residue is taken up in diethyl ether, and the solution is washed with 2N hydrochloric acid solution (25 mL), 2×25 mL of 10% sodium carbonate solution, brine, dried (magnesium sulfate), and evaporated leaving 5.6 g of a crude viscous oil which crystallizes on standing. Recrystallization from 60 mL of 2:1 isooctane:toluene affords 3.9 g of the title compound as tan crystals; mp 99°–101° C.

EXAMPLE 17

5-[4-{Acetylamino)-2,5-dimethylphenoxy]-2,2-dimethylpentanoic acid, methyl ester A mixture of 3.1 g (10 mmol) of the 5-(2,5-dimethyl-4-nitrophenoxy)-2,2-dimethylpentanoic acid, methyl ester (Example 1) and 2.0 g (3.5×10 mg-atom) of iron powder (40 mesh) in 35 mL of glacial acetic acid is stirred at reflux for 1.5 hours and poured into an ice-water mixture (300 mL). After scratching the oil crystallizes and the solid is collected on a filter, washed with water, and dried in vacuo at 40° C. The filtrate is extracted with dichloromethane. The extracts are washed with water, dried (magnesium sulfate), filtered, and evaporated leaving a medium brown oil which partially crystallizes. Recrystallization from 75 mL of isopropyl ether in the presence of charcoal affords 1.0 g of the title compound; mp 99°–100° C.

PREPARATION OF STARTING MATERIALS

EXAMPLE A

4-Nitro-2,5-Xylenol

Step A: Preparation of 4-Nitroso-2,5-xylenol

A solution of 20 mL of 36N sulfuric acid solution in 40 mL of water (60 mL of 12N sulfuric acid) is added to a mixture of 61 g (500 mmol) of 2,5-xylenol and 200 mL of glacial acetic acid. A homogeneous solution is produced initially, but on continued stirring some of the phenol crystallizes. A solution of 35 g (500 mmol) of sodium nitrite in 60 mL of water is added dropwise to the previous mixture over 60 minutes at 5° to 10° C. Stirring is continued for 10 to 15 minutes and the heterogeneous mixture is poured into 1 L of water. The reaction flask is rinsed with water and the solid nitroso derivative collected, washed with water, and dried to a moist cake.

Step B: Preparation of 4-Nitro-2,5-xylenol

The moist nitroso derivative is divided into two portions and each is added to a 70% solution of nitric acid and warmed to 45° C.±5° C. After addition of the first portion, nitrogen oxide fumes are evolved, and after a 10-minute interval the second portion is added. The heterogeneous mixture is stirred at 45° C.±5° C. for a total of 1 5 hours, added t◯1 L of water, and the title compound collected, washed thoroughly, and air dried to give 76 g. Recrystallization from toluene-isoctane affords the title compound as yellow leaflets; mp 121°–123° C.

I claim:

1. A compound selected from the group consisting of:

5-[2,5-Dimethyl-4-[[(4-methylphenyl)-sulfonyl]amino]phenoxy]-2,2-dimethylpentanoic acid, methylester;

5-[4-[(Hexadecylsulfonyl)amino]-2,5-dimethylphenoxy]-2,2-dimethylpentanoic acid, methyl ester;

5-[2,5-Dimethyl-4-[[(phenylmethyl)sulfonyl]-amino]phenoxy]-2,2-dimethylpentanoic acid, methyl ester;

5-[4-[[(4-Fluorophenyl)sulfonyl]amino]-2,5-dimethylphenoxy]-2,2-dimethylpentanoic acid, methyl ester;

5-[2,5-Dimethyl-4-[(2-naphthalenylsulfonyl)-amino]phenoxy]-2,2-dimethylpentanoic acid, methyl ester;

5-[4-[[(2,5-Dichlorophenyl)sulfonyl]amino]-2,5-dimethylphenoxy]-2,2-dimethylpentanoic acid, methyl ester;

2,2-Dimethyl-5-[2,5-dimethyl-4-[[(2,4,6-trimethylphenyl)sulfonyl]amino]phenoxy]pentanoic acid, methyl ester;

5-[4-(Benzoylamino)-2,5-dimethylphenoxy]-2,2-dimethylpentanoic acid, methyl ester;

5-[2,5-Dimethyl-4-[(methylsulfonyl)amino]-phenoxy]-2,2-dimethylpentanoic acid, methyl ester;

5-[4-[[(4-Methoxyphenyl)sulfonyl]amino]-2,5-dimethylphenoxy]-2,2-dimethylpentanoic acid, methyl ester;

5-[4-[[[(2,4-Difluorophenyl)amino]carbonyl]-amino]-2,5-dimethylpenoxy]-2,2-dimethylpentanoic acid, methyl ester;

5-[4-[[[[2,6-Bis(1-methylethyl)phenyl]amino]-carbonyl]amino]-2,5-dimethylphenoxy]-2,2-dimethylpentanoic acid, methyl ester; and 5-[2,5-Dimethyl-4-[[(phenylamino)-thioxomethyl]amino]phenoxy]-2,2-dimethylpentanoic acid, methyl ester.

2. A method of treating hypercholesterolemia or atherosclerosis comprising administering to a mammal in need of such treatment an acyl-coenzyme A:cholesterol acyltransferase-inhibitory effective amount of a compound as defined in claim 1 in unit dosage form.

3. A pharmaceutical composition for treating hypercholesterolemia or atherosclerosis comprising an acyl-coenzyme A:cholesterol acyltransferase-inhibitory effective amount of a compound as defined in claim 1 in combination with a pharmaceutically acceptable carrier.

* * * * *